United States Patent [19]
Ewart et al.

[11] Patent Number: 5,922,537
[45] Date of Patent: Jul. 13, 1999

[54] NANOPARTICLES BIOSENSOR

[75] Inventors: Thomas G. Ewart, King City; Gavin T. Bogle, Toronto, both of Canada

[73] Assignee: NøAB Immunoassay, Inc., Markham, Canada

[21] Appl. No.: 08/746,420

[22] Filed: Nov. 8, 1996

[51] Int. Cl.⁶ .............. C12Q 1/68; C12Q 1/70; G01N 33/53; G01N 33/537

[52] U.S. Cl. .............. 435/6; 435/5; 435/7.1; 435/7.92; 435/7.93; 536/501; 536/518; 536/524; 536/525; 536/526; 536/527; 536/532; 536/536

[58] Field of Search ............. 435/6, 5, 7.1, 7.92, 435/7.93; 422/68.1; 436/501, 536, 518, 524, 527, 532, 526, 525

[56] References Cited

U.S. PATENT DOCUMENTS

| | | |
|---|---|---|
| 4,219,335 | 8/1980 | Ebersole . |
| 4,454,007 | 6/1984 | Pace . |
| 4,510,436 | 4/1985 | Raymond . |
| 4,731,337 | 3/1988 | Luotola et al. . |
| 4,766,062 | 8/1988 | Diamond et al. ............ 435/6 |
| 4,769,121 | 9/1988 | Newman ................... 204/403 |
| 4,797,363 | 1/1989 | Teodorescu et al. ........ 435/235 |
| 4,822,566 | 4/1989 | Newman . |
| 4,824,529 | 4/1989 | Thompson et al. . |
| 4,857,273 | 8/1989 | Stewart . |
| 4,880,752 | 11/1989 | Keck et al. . |
| 4,925,788 | 5/1990 | Liberti . |
| 4,999,284 | 3/1991 | Ward et al. . |
| 5,001,048 | 3/1991 | Taylor et al. . |
| 5,104,791 | 4/1992 | Abbott et al. . |
| 5,156,972 | 10/1992 | Issachar .................... 435/288 |
| 5,192,507 | 3/1993 | Taylor et al. . |
| 5,196,306 | 3/1993 | Bobrow et al. . |
| 5,262,299 | 11/1993 | Evangelista et al. . |
| 5,344,784 | 9/1994 | Attridge . |
| 5,403,484 | 4/1995 | Ladner et al. . |
| 5,427,908 | 6/1995 | Dower et al. . |
| 5,432,018 | 7/1995 | Dower et al. . |
| 5,447,845 | 9/1995 | Chu et al. . |
| 5,464,741 | 11/1995 | Hendrix . |
| 5,501,986 | 3/1996 | Ward et al. . |
| 5,516,637 | 5/1996 | Huang et al. . |
| 5,674,698 | 10/1997 | Zarling et al. ............ 435/7.92 |

FOREIGN PATENT DOCUMENTS

| | | |
|---|---|---|
| 1275533 | 10/1990 | Canada . |
| 2070572 | 12/1992 | Canada . |
| 1336758 | 8/1995 | Canada . |
| 3-188374 | of 1991 | Japan . |
| 4-72564 | of 1992 | Japan . |
| 2 136 130 | 9/1984 | United Kingdom . |
| WO 87/03095 | 5/1987 | WIPO . |
| WO 88/08528 | 11/1988 | WIPO . |
| WO 89/11649 | 11/1989 | WIPO . |
| WO 91/02811 | 3/1991 | WIPO . |
| WO 92/01787 | 2/1992 | WIPO . |
| WO 92/21768 | 12/1992 | WIPO . |
| WO 92/21976 | 12/1992 | WIPO . |
| WO 93/03356 | 2/1993 | WIPO . |
| WO 94/02852 | 2/1994 | WIPO . |
| WO 94/08221 | 4/1994 | WIPO . |
| WO 94/11735 | 5/1994 | WIPO . |
| WO 94/28414 | 12/1994 | WIPO . |
| WO 95/27081 | 10/1995 | WIPO . |
| WO 96/15450 | 5/1996 | WIPO . |

OTHER PUBLICATIONS

Bataillard et al, *Analytical Chemistry*, vol. 60, No. 21, (1988) 2374–2379.

DeSilva et al., *Biosensors & Bioelectronics*, 10, (1995) 675–682.

Kasapbasioglu et al., *Sensors and Actuators* B, 13–14 (1993) 749–751.

*Primary Examiner*—Stephanie W. Zitomer
*Attorney, Agent, or Firm*—Fish & Richardson, P.C., P.A.

[57] ABSTRACT

Biosensor technology based on the labelling entities having particle reporters provides cost competitive readily manufactured assay devices. Sub-micron particles of uniform dimension in metals, polymers, glasses, ceramics and biological structures such as phages are used as the labelling entities. Such reporter particles greatly increase the sensitivity and accuracy, and provide a variety of assay techniques for determining analyte presence in a sample. The particles may have dielectric, paramagnetic and/or phosphorescent properties, such particles are particularly useful in a variety of competition type assays. Novel phosphor and phage particles are provided for use as unique labelling entities.

13 Claims, 12 Drawing Sheets

NANOPARTICLES BIOSENSOR

SCOPE OF THE INVENTION

This invention relates to a biosensor for use in determining analyte presence or concentration in a sample. The biosensor includes a test surface which may be used in a variety of assay techniques, such as competition assays, sandwich assays, direct and indirect assays, hybridization assays and the like. The use of uniform size, preferably sub-micron particles of metals, polymers, glasses, ceramics, phages and the like having dielectric, paramagnetic or phosphorescent properties provide a cost competitive, readily manufactured, easy to use assay devices. The test surfaces of the devices may be manufactured in a manner which only require the addition of a sample for purposes of determining suspected analyte in a sample. The test surface is designed to determine analyte concentration by virtue of addition or displacement of the labelling entities to or from the test surface so that a change in label signal can be detected. The particle reporters may be dielectric particles, paramagnetic particles, phosphorescent particles, phages and phages incorporating reporter material. Novel particles for use in various assays include phage reporter particles and phage reporter particles which express on their surface or incorporate solid phase materials or molecules which provide dielectric properties, magnetic properties, phosphorescent properties and mixtures thereof.

BACKGROUND OF THE INVENTION

The greatest challenge in the biosensor industry is to detect in a meaningful commercially viable manner assay reactions which take place at the molecular level. There are many situations where the detection of analyte in sample at concentrations in the picomolar range may be indicative of a particular condition in microorganisms and higher life forms, including of course animals and humans. Such demands have driven the biosensor industry towards very sophisticated and elaborate assay schemes to achieve such minute detections. However, such devices are normally too expensive to manufacture, sell and use and hence are not readily received by the research and health care communities.

Various assays which involve amplification of the signal have been effective in sensing picomolar concentrations. However, such amplification involves fairly elaborate chemistry, several sample handling and washing steps and very sophisticated sensing technology such as fluorometric detection. An example of such fluorometric amplification is described in U.S. Pat. No. 5,262,299 entitled Enzyme-Amplified Lanthanide Chelate Luminescence.

Other attempts to achieve an amplified signal indicating presence of analyte, involves the use of particles, normally polymeric, gold, solid and porous glass particles of the micron and sub-micron size. Detection based on the presence of such particles involves the use of filters, capacitance, fluorescence, magnetic separation and the like. In order to achieve the desired sensitivities in using such particles in biosensors it has been a requirement that the operation of the test device be closely controlled. Quite often the sensitivities in using such particles in biosensors it has been a requirement that the operation of the test device be closely controlled. Quite often the sensitivities in these various types of biosensors are greatly altered by minor external changes such as in temperature, pressure, flow rates, sample introduction and washing times and the like. Even with special care in providing instrument stability it is still not possible to detect changes at the molecular level where just a few molecules are detected.

Phosphorescent properties have been sensed in various types of assays, particularly with the use of metalloporphyrins. Such compounds are encapsulated in liposomal vesicles or entrapped in polymer latex particles and bound adhesively or covalently to antibodies. The significant disadvantage in the use of porphyrin based phosphors is that the phosphorescence is quenched by oxygen in aqueous media. An attempt to eliminate this quenching is desired in U.S. Pat. No. 5,464,741 where a complex formation with the porphyrin is made.

U.S. Pat. No. 4,219,335 describes the use of reactance tags in form of small particles which by virtue of capacitance measurement provides a determination of whether or not analyte is present in the sample. The system is particularly adapted to the use of magnetic particles where the presence of the magnetic particles is measured as a change in inductance.

A more sophisticated capacitance type measurement is described in U.S. Pat. No. 4,822,566. Particles however are not used as labelling entities. Instead, the presence or absence of the complexed antibodies is detected by way of a capacitance type measurement to determine analyte concentration. However, such system is not reliable from a sensitivity standpoint and must be calibrated for each different analyte to be measured. In addition, liquid handling in this system becomes crucial.

The test system and particles used in the biosensor of this invention overcomes a number of the above problems and at the same time provides an assay system which is sensitive at the sub-picomolar or less range. Experience with current high volume automated instruments in the diagnostic field has demonstrated that 70 to 90% of the robotic cost, complexity, repeat testing, and electromechanical breakdown is related to liquid handling. The system of this invention may be reagentless or reagents-contained in the assay device in which only one liquid handling step is required during introduction of the sample to the device. The device includes a test surface which readily lends itself to simplified robotics.

SUMMARY OF THE INVENTION

According to an aspect of the invention, a displacement competition assay, comprises minimum fluid handling, for determining sample analyte concentration in a sample fluid, wherein:

i) the sample fluid is applied to a test surface having a second analyte reversibly bound through specific recognition sites to a first analyte, wherein the first analyte is irreversibly affixed to a solid support and the second analyte is labelled with reporter particles selected from the group consisting of dielectric particles, paramagnetic particles, phosphorescent particles, particles having a combination of at least two of dielectric, magnetic and phosphorescent properties, phages, phages encapsulating reporter particles and mixtures thereof, the reporter particles providing a base level signal; and ii) the sample analyte competes for binding to at least one of the specific recognition sites wherein binding of the sample analyte to the specific recognition site displaces the labelled second analyte away from the test surface into the sample fluid to define a test level signal; and wherein displacement of the labelled second analyte is related to the concentration of sample analyte in the sample fluid; and the iii) the same fluid is removed from the test surface; and iv) the base level signal is compared to the test level signal to determine the concentration of the sample analyte; and v) the minimum fluid handling is achieved by virtue of providing a prepared test surface and providing means for the sample fluid to be withdrawn subsequent to contact with the test surface.

According to another aspect of the invention, the use of phage particles encapsulating reporter particles in an assay to detect the presence or quantity of a suspected analyte in a test sample by use of an analyte recognition molecule.

According to a another aspect of the invention, the use of phage particles encapsulating reporter particles in an assay format selected from the group consisting of competition assay, sandwich immunoassay, direct immunoassay, indirect immunoassay and nucleotide hybridization assays.

According to a further aspect of the invention, a method of preparing phage particle diagnostic reagents wherein:

i) the phage particle is disrupted ii) nucleic acids are moved to provide a depleted particle iii) reporter molecules are inserted into the depleted particle iv) the particle is reassembled around the reporter molecule.

BRIEF DESCRIPTION OF THE DRAWINGS

Various aspects of the invention are described with respect to the drawings wherein.

DETAILED DESCRIPTION OF THE PREFERRED EMBODIMENTS

In accordance with this invention, particle reporters are provided as labelling entities for use in a variety of biosensors. The particle reporters greatly enhance the sensitivity of the biosensors and are capable of detecting the addition or substraction of a single particle reporter to or from the test surface. This advantage of the invention is due in part to the uniform dimensioned minute particles of micron and nanometer size. The reporter particles may be selected from the group consisting of dielectric particles, magnetic particles, solid-phase phosphor particles, particles having a combination of at least two of dielectric, magnetic and phosphorescent properties, phages, phage incorporating reporter material and mixtures thereof. The reporter particles can be used in a variety of assays which include competition, sandwich, direct, indirect immunoassays and nucleic acid hybridization assays. Exemplary immunoassays which involve the use of analyte recognition molecules for recognizing analyte in the sample are shown in FIGS. 1 and 2.

Figure 1A:
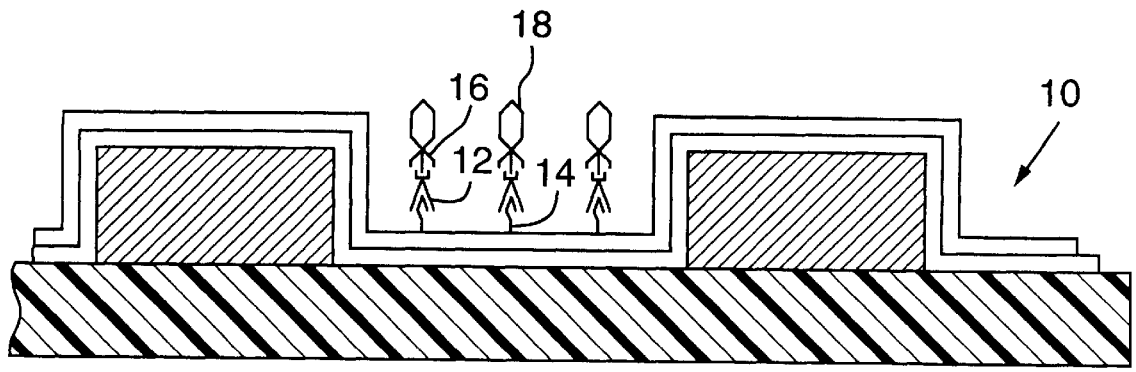
FIGS. 1A through 1C show the use of particles in a competition assay.

In FIG. 1A is a competition assay is shown where a test surface 10 has analyte entities referred to as a first analyte 12 linked to the test surface 10 by linking components 14. The analyte recognition molecule or second analyte 16 has a reporter particle 18 which as the labelling entity is attached to the second analyte 16. The first analyte 12 may be the same as the sample analyte to be detected or may be a fragment or some other analog thereof. The first analyst 12 may have the same binding affinity for the second analyte 16 or may have a greater or lesser binding affinity than the analyte in the sample for the second analyte 16.

Figure 1B:
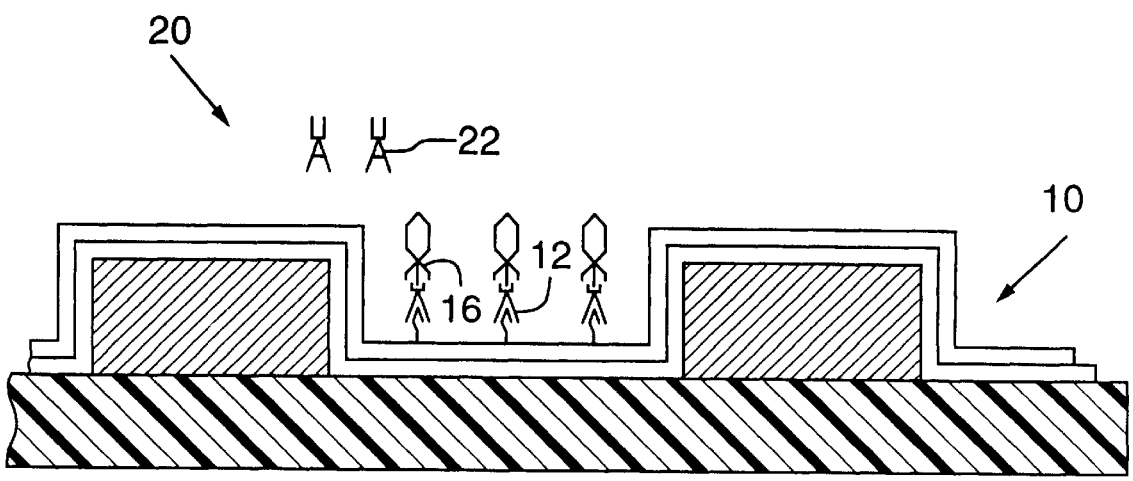
Figure 1C:
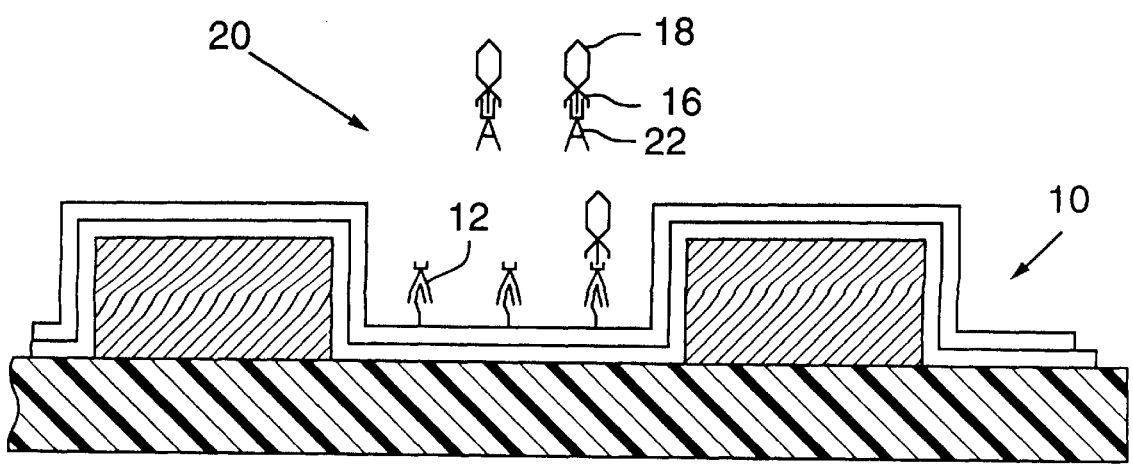

In FIG. 1B the sample fluid 20 is introduced and contains sample analyte 22. Sample analyte 22 competes with the first analyte 12 for the labelled second analyte 16. The concentration of the sample analyte 22 in the sample 20 determines the sample extent to which the first analyte molecules 22 displace the analyte entities 12 from the second analyte entities 16 so as to compete with the first analyte entities in binding to the second analyte entities 16. As shown in FIG. 1C the second analyte 22 in the sample has competed with the first analyte entities 12 to displace the reporter particles 18 away from the test surface 10. Such displacement of the reporter particles from the test surface results in a measurable difference, hence determining through suitable controls of the and biosensors, both a qualitative and quantitative measure of the analyte present in the sample.

Figure 2A:
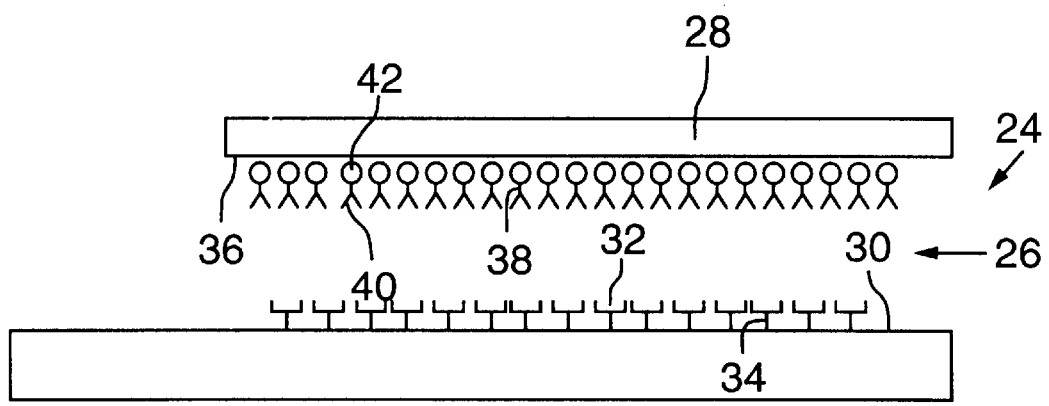
FIGS. 2A through 2C show the use of phosphor particles in a sandwich assay.
Figure 2B:
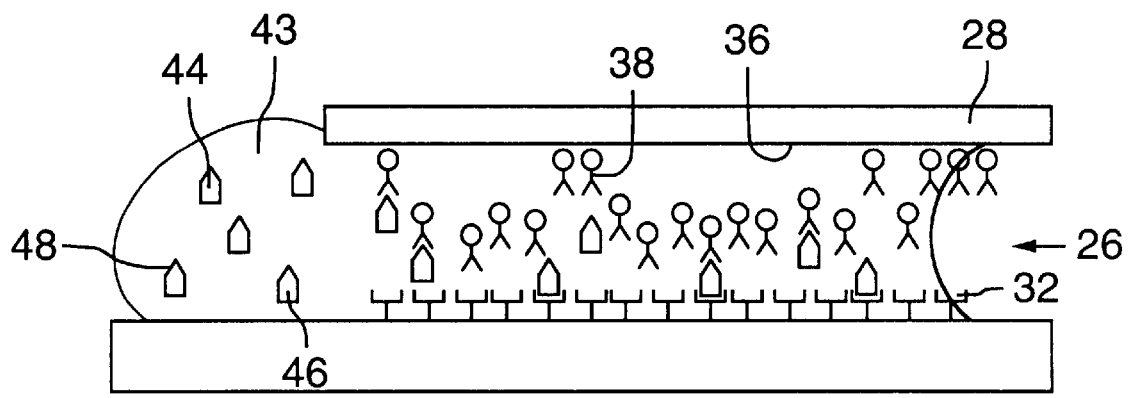
Figure 2C:
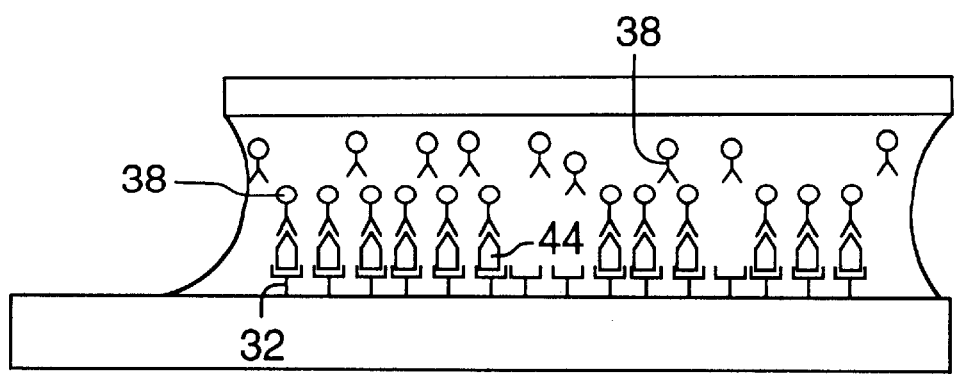

As shown in FIG. 2, a biosensor 24 has a capillary space 26 defined between biosensor plate 28 and test surface 30. The test surface is a layer of recognition molecules 32 linked to the surface 30 by linkers 34. On the undersurface 36 of the plate 28 is a dried film of labelling entities 38 which comprise antibodies 40 having linked thereto reporter particles 42. When sample is introduced to the capillary space 26, which may be a drop of whole blood 43, the blood 43 is drawn into the capillary space 26 by capillary attraction. The presence of the blood dissolves the labelling entities 38 form the underside 36 of plate 28. The analyte 44 in the sample has a site 46 which is recognized by the analyte recognition molecules 32 and a site 48 which is recognized by the antibodies 40. The analyte 44 is then sandwiched between the recognition molecules 32 and the fixed antibodies 38. As the sample is incubated in the biosensor 24, analyte molecules 44 are bound to the recognition molecules 32 and are correspondingly labelled with the particle reporters 40. By virtue of the antibodies recognizing the sites 48 on the analyte, the particle reporters are immobilized on the test surface 30. Such sandwich assay then provides in an appropriate biosensor, a measure of analyte present on the test surface 30.

The use of uniform size nanoparticles or micron particles as particle reporter can provide in suitably calibrated biosensor, a measure in terms of presence or absence of the reporter particles down to a level of one reporter particle. By selecting the properties of the reporter particle, its dielectric paramagnetic or phosphorescent properties can be enhanced relative to the sensing conditions of the biosensor. It is now possible to obtain in nanoparticle size a variety of particles made from ceramics, metal oxides, plastics, glasses and the like. Kossovsky et al. U.S. Pat. No. 5,219,577 describes ruthenium oxide, tin oxide and glass nanoparticles which may be coated with cellobiose in forming a strong adhesive bond with glass ceramic nanostructures. These structures which can be derivatized, may be reacted with proteins, lipoproteins, glycoproteins, drugs, heptens, oligonucleotides and the like. With nanoparticles the activity of the various biological molecules attached thereto is normally retained. Another suitable linking technique is described in U.S. Pat. No. 5,429,824 where tyloxapole is used as a nanoparticle stabilizer and dispersant. The core particles may be made from a wide variety of inorganic materials including metals or ceramics. Preferred metals include chomium, rubidium, iron, zinc, selenium, nickel, gold, silver, platinum. Preferred ceramic materials include silicon dioxide, titanium dioxide, aluminum oxide, ruthenium oxide and tin oxide. The core particles may be made form organic materials including carbon (diamond). Preferred polymers include polystyrene, nylon and nitrocellulose. Particles made from tin oxide, titanium dioxide or carbon (diamond) are particularly preferred).

Particles made from the above materials having diameters less than 1000 nanometers are available commercially or they may be produced from progressive nucleation in solution (colloid reaction), or various physical and chemical vapour deposition processes, such as vacuum sputtering deposition (Hayashi, C., *J. Vac. Sci. Technol.* A5(4), July/August 1987, pgs. 1375–1384; Hayashi, C., *Physics Today*, December 1987, pgs. 44–60, MRS Bulletin, January 1990, pgs. 16–47). Tin oxide having a dispersed (in $H_2O$) aggregate particle size of about 140 nanometers is available commercially from Vacuum Metallurgical Co. (Japan). Other commercially available particles having the desired composition and size range are available from Advance Refractory Technologies, Inc. (Buffalo, N.Y.).

Plasma-assisted chemical vapour deposition (PACVD) is one of a number of techniques that may be used to prepare suitable microparticles. PACVD functions in relatively high atmospheric pressures (on the order of one torr and greater) and is useful in generating particles having diameters of up to 1000 nanometers. For example, aluminum nitride particles having diameters of less than 1000 nanometer can be synthesized by PACVD using $Al(CH_3)_3$ and $NH_3$ as reactants. The PACVD system typically includes a horizontally mounted quartz tube with associated pumping and gas feed systems. A suspector is located at the centre of the quartz tube and heated using a 60 $KH_z$ radio frequency source. The synthesized aluminum nitride particles are collected on the walls of the quartz tube. Nitrogen gas is used as the carrier of the $Al(CH_3)_3$. The ratio of $Al(CH_3)_3$:$NH_3$ in the reaction chamber is controlled by varying the flow rates of the $N_2/Al(CH_3)_3$ and $NH_3$ gas into the chamber. A constant pressure in the reaction chamber of 10 torr is generally maintained to provide deposition and formation of the ultrafine nanocrystalline aluminum nitride particles. PACVD may be used to prepare a variety of other suitable nanocrystalline particles.

Paramagnetic materials are described in nanoparticle form in U.S. Pat. Nos. 5,468,427 and 5,523,065. The ceramic nanoparticles are substantially homogeneous in composition and in diameter and may be of the order of 300 nm is size. A larger number of metal semi-conductor and lanthanide metal oxide nanoparticles may be produced by the method of this U.S. patent including $SiO_2$ nanoparticles.

The core particles are optionally coated with a substance that provides a threshold surface energy to the particle sufficient to cause binding to occur without that binding being so tight as to denature biologically relevant sites. Coating is preferably accomplished by suspending the particles in a solution containing the dispersed surface modifying agent. It is necessary that the coating make the surface of the particle more amendable to protein or peptide attachment. Suitable coating substances in accordance with the present invention include cellobiose, related basic sugars, and modified sugars such as nitrocellulose. Oligonucleotides may also be used. Suitable oligonucleotides include polyadenosine (poly A). Cellobiose is a preferred coating material.

The coating solution into which the core particles are suspended contains, for example, from 1 to 30 weight/volume percent of the coating material. The solute is preferably double distilled water ($ddH_2O$). The amount of core particles suspended within the coating solution will vary depending upon the type of particle and its size. Typically, suspensions containing from 0.1 to 10 weight/volume percent are suitable. Suspensions of approximately 1 weight/volume percent of particles are preferred.

The core particles are maintained in dispersion in the coating solution for a sufficient time to provide uniform coating of the particles. Sonication is the preferred method for maintaining the dispersion. Dispersion times ranging from 30 minutes to a few hours at room temperature are usually sufficient to provide a suitable coating to the particles. The thickness of the coating is preferably less than 5 nanometers. Thicknesses of the coating may vary provided that the final core particles include a uniform coating over substantially all of the particle surface.

The particles are separated from the suspension after coating and may be stored for future use or redispersed in a solution containing the protein or peptide to be attached to the particles. Alternatively, the coated particles may be left in the suspension for further treatment involving attachment of the desired protein or peptide.

In particular, surface active agents for modifying nanoparticle surface properties through adsorptive coating involve the use of cellulose derivatives such as methyl, carboxymethyl, hydroxyethyl, hydroxypropyl and hydroxypropylmethyl as used in the preparation of derivatized nanoparticles.

Covalent linkers for nanoparticles involve covalent immobilization of protein, glycosidic and lipidic structure to the solid phases. Such techniques preserve the tertiary structure and biochemical function of the analyte entity and/or recognition molecules. Preferably, they orient the recognition molecules in such a way as to favour their complex formation, such as described in the linking entity used in Newman U.S. Pat. No. 4,822,566.

Commonly, —OH functional groups are introduced to the surfaces of glasses, (eg. $SiO_2$), semiconductors, metal oxides, metals and polymers by treatment of the surfaces under acid conditions as described in U.S. Pat. No. 4,824,529. These —OH groups readily react with trifunctional silanes such as (3-aminopropyl) triethoxysilane or 3-glycidoxypropyltrimethoxysilane, or with monofunctional aminosilanes such as (4-aminobutyl) dimethylmethoxysilane, or with thiol-terminal silanes, such as mercaptomethyldimethylethoxysilane, or trihexylchlorisilane, the latter by nucleophilic displacement of the chlorine. The linkers are available commercially from such suppliers as Fluka (Haupage, N.Y.), Aldrich (Milwaukee, Wis.), and Petrach Systems (Bristol, Pa.). To these amino- or thiol-terminal silanes one may graft the desired peptide, lipidic, or glycosidic moeity via homobifunctional crosslinkers such as glutaraldehyde, or via heterobifunctional crosslinkers such as N-γ-maleimidobutyryloxy succinamide ester (GMBS) (Calbiochem, San Diego, Calif.), N-succinimidyl-3(2-pyridyldithio)propionate (SPDP) (Pierce, Rockford, Ill.). Synthetic peptides, and libraries may be grown on these silane-derivatized solid phase particles and surfaces by any of the peptide synthesis chemistries (eg. t-BOC, FMOC chemistries) which are based mostly on the reaction of active ester intermediates of N-protected amino acids or amino acid analogs in solution phase with deprotected amino acids linked to a solid phase (SiO, sepharose, etc.)

The particles can be bonded to recognition molecules, analyte or analyte entities by known techniques. The particle reporters can be encapsulated with an organic polymer to which the immune compounds can be bonded, or the particle surface can be silanized by conventional techniques as described above. Organic compounds can then be attached to the silane linkage. U.S. Pat. No. 3,954,666 teaches polymer encapsulation of core materials and U.S. Pat. No. 3,983,299 teaches the use of silane linkages to bond organic compounds to inorganic particles. Techniques for immobilization of enzymes on magnetic supports which would be equally applicable to antibodies are described in *Enzymology*, XLIV pp. 324–326. Other bonding methods may also be used so long as they do not interfere with the complexing ability of the recognition molecules. The recognition molecules may be chosen to be specifically reactive with either the analyte or with the complex of the analyte with another recognition molecule.

The receptor molecule can be attached to the test surface by surface adsorption, gel entrapment, covalent bonding or other similar methods. Of these, covalent bonding is preferred. Any system of recognition molecule attachment capable of orienting the molecules on the test surface so that they will have maximum activity is also preferred. Recognition molecules include not only antibodies, but also tissue or cellular receptor proteins, serum transport proteins, binding proteins, peptides, DNA, RNA and lectins. Of these, antibodies probably have the widest applicability. Other classes of compounds, such as chelating agents, may also serve as useful receptor reagents if they react with the substance to be determined in the body fluid with sufficient specificity to avoid false results caused by competing reactions.

The binding agent that forms the biochemical binding system an be selected from general or specific affinity ligands and may include, but is not limited to, antibodies, binding proteins, lectins, enzymes and receptors. The immobilized analyte which forms the first layer of the biochemical binding system may be the same molecular substance as the analyte under test, or it may be an analog of the analyte that is biospecific to the binding agent. The immobilized analyte may, for example, be an antigen, a hapten, a polysaccharide, a glycoprotein, a glycolipid, an enzyme inhibitor, an enzyme substrate, a neurotransmitter, a hormone and the like. Table I contains examples of the biochemical binding systems which may be used in a competitive binding embodiment to test for a particular analyte.

TABLE I

| Immobilized analyte | Binding Agent | Analyte | Class of Sensor |
|---|---|---|---|
| antigen | antibody | antigen | A |
| hapten | antibody | hapten | A |
| polysaccharides | lectin | polysaccharides | B |
| glycoproteins | lectin | glycoproteins | B |
| glycolipids | lectin | glycolipids | B |
| enzyme inhibitor | enzyme | enzyme inhibitor | C |
| enzyme substrate | enzyme | enzyme substrate | C |
| enzyme inhibitor | enzyme | enzyme substrate | C |
| neurotransmitters | neural receptor | neurotransmitters | D |
| hormones | tissue/neural receptor | hormones | D |
| proteins | single & double stand DNA & RNA | protein DNA, RNA | E |
| vitamins | binding proteins or DNA | vitamins | E |
| DNA | DNA/Antibody | DNA/RNA | E |
| RNA | RNA/Antibody | DNA/RNA | |

As can be seen from Table I, there are four classes of the competitive binding sensors. In Class A the binding agent is an antibody specific to the analyte. The analyte may be an antigen or hapten. The biochemical binding system comprises a first immobilized layer of the antigen or hapten analyte with a second layer of the biospecific antibody biochemically bound to the immobilized analyte in the first layer.

In class B, the binding agent is a lectin, which is a general ligand specific to a group of analytes. A lectin-based sensor can be made more specific by an appropriate molecular sieve membrane that excludes larger molecules in the general analyte group from reacting with the biochemical binding system. In this class, for example, the binding system could have a first immobilized layer of polysaccharide or a membrane protein containing sugar residues of certain configurations and a second layer of the general lectin bound to the first layer.

In class C, the binding agent is an enzyme reactive with an enzyme inhibitor or enzyme substrate. In this class, for example, the binding system could have an inhibitor for a particular enzyme immobilized on the sensor surface and a second layer containing the enzyme bound to the inhibitor in the first layer. With a particular enzyme substrate in the test fluid, the enzyme binding agent will be drawn from the surface of the binding system.

In class D, the binding agents are neuroreceptors and tissue receptors. The receptor has its molecular conformation greatly altered by various neutrotoxins and other agents. The binding system can have a layer of succinylcholine immobilized on the sensor surface with a second layer of acetylcholine receptor molecules bound to the first layer. If neurotoxins, for example, is present in the test fluid, the receptor binding behaviour will be altered and it will be released from the binding system surface, thereby altering the dielectric properties of the sensor. It is of course to be understood that these are merely examples of the biochemical binding systems that can be used with the competitive binding embodiment of the present invention.

In class E, DNA/RNA are the binding agents to which targeted DNA/RNA hybridizes. It is also understood that it is now possible to raise certain types of antibodies to nucleic acid sequences and that there are specific DNA and RNA binding proteins, such as "zinc-finger" proteins. Hence, the binding agent may also be an antibody. The target DNA/

RNA (analyte) may encode known proteins, vitamins and fragments thereof.

Molecules of a binding agent 16 are immobilized on the passivation layer on test surface with linking molecules 14. In FIG. 1A, the layer of the immobilized binding agent coats the entire passivation surface 10. The binding agent is an affinity ligand that will bind specifically to the analyte, such as an antibody binds specifically to a particular virus or as an antigen binds specially to a particular antibody. Alternatively, the affinity ligand may bind to a specific group of analytes, such as nucleotide analogs and lectins bind to certain groups of biochemical analytes.

The materials useful as capacitance particle reporters which combine with recognition molecules or analyte entities are those which will alter the electrical reactance of the test surface. That is, these materials, if distributed as a finely divided powder on the test surface, alter the dielectric, conductive or the magnetic properties of the surface. The advantage of this invention resides in using particles which are detectable in very small quantities by very sensitive but well developed and readily available electrical components. Further, the use of such materials avoids the problems of transient activity and handling hazards which one encounters in the use of radioactive tags. The preferred materials for detection by inductive reactance are metals and metal oxides which exhibit paramagnetism. Such materials can be bound to antibodies and applied to the test surface while in a demagnetized state. Once they have been applied, the entire surface can be exposed to a magnetic field to magnetize the particles for detection purposes. This magnetic activity is then readily detectable by various well-known means such as a standard magnetic tape read head or Hall effect detector. Magnetic materials include, but are not limited to, metals and alloys such as iron powder, nickel, cobalt, $CrO_2$, "Ferrofluid" (a ferromagnetic liquid produced by Ferrofluids Corp.), CoO, NiO, $Mn_2O_3$, magnetoplumbites, magnetic iron oxides and "Alnico", an alloy of aluminum, nickel, cobalt and copper. Other useful materials are organic charge complexes with the high electrical conductivity such as N-methylphenazium tetacyanoquinodimethane, $[Ce(NO_3)_6Mg(H_2O)_6]_3 \cdot 6H_2O$ crystal, $Bi_2Se_3$ crystals and tetrathiofulvalene complexes with tetracyano-p-quinodimethane or $K_2Pt(CN_4)BrO_3 \cdot H_2O$ and amorphous materials with magnetic properties such as the chalcogenides, e.g., the europium chalcogenides and chalcogenide glass particles.

Preferred magnetic materials are the magnetic oxides of iron, cobalt, nickel, chromium and manganese and oxide coated particles of iron or nickel.

The solid phase phosphor particles for use in this invention have been available for many years and are commonly used in the coating of cathode ray or of television tubes. The solid phase phosphor particles may be made in the micro or nanoparticle size. Suitable solid phase phosphors may be selected from the following group:

Phosphors which can be represented by the formula $MAl_2O_4$ in which M is a metal from the group Ca, Sr and Ba, or in which M is Mg in combination with one or more of Ca, Sr, or Ba with Eu as "activator".

ZnS phosphor pigment in a polymerized PVC resin with zinc-based primary stabilizer, tertiary organic phosphite as a secondary stabilizer, epoxidized soybean oil as primary plasticizer, and secondary plasticizer selected from pthalates, adipates, trimellitates, azelates, and phosphates.

Phosphors which can be represented by the formula $M_2AOF_5$ where M is K, Ru or Cs, and A is Ta, or Nb.

Polymorphous phosphorescent compounds which can be represented by the formula $MNbOF_5$ where M is one or more of Ba, Sr, Pb, and Ca.

Polymorphous phosphorescent compounds which can be represented by the formula $MWO_2$ where M is one or more of Ba, Sr, or Pb.

Phosphorescent compounds which can be represented by the formula $Pr_xSrM_{1-x}AlO_4$ where Pr is praseodymium, M is La (Lanthanum III) or Ga (Gadolinium III), and X is in the range 0.025 to 0.075.

Phosphorescent compounds which can be represented by the formula $NaY_{1-x}A_xM_2O_6$ where A is Eu, or Bi (bismuth), M is Zr (Zirconium) or Ha (Hafnium), and X is in the range of 0.001 to 0.25.

An organ phosphor which is a solid insoluble in water and organic solvents comprises of molecules of at least one phosphorescent activator held within a matrix of a condensation resin that does not have an absorbtion spectrum overlapping that of the phosphor's excitation or emission bands. The phosphor activator is/are a compound or mixtures of compounds of the general formula $(A)_m$-Ar—CO—X, where Ar denotes a fused ring polycyclic aromatic group; m is zero or an integer of from 1 up to the maximum number of ring positions available for substitution; X denotes an alkyl group or a group of the formula $(A)_m$-Ar— or $(B)_n$Ph-, where Ph is a phenyl group and n is zero or an integer of from 1 to 5; and A and B represent ring substituents, or an acid addition salt thereof when said compound is basic.

An infrared light excitable phosphor prepared from a base, first and second dopants, a carbonate of the base, and a fusible salt. The base is an alkaline earth metal sulphide such as CaS or SrS. $CaCO_3$ or $SrCO_3$ is the corresponding carbonate of the said base and LiF is used to allow the material to be fused together. Samarium oxide, and Europium oxide are used as the first and second dopants for establishing the infrared wavelength and an electron trapping level respectively.

Phosphors based upon a crystalline matrix of an alkaline earth and a chalcogen together with an activator prepared from both Se and S vapours. An activator is Eu:Cu. IR-stimulable phosphors have quantum efficiencies above 5%, and activators include Eu:Sm or Eu:Bi.

Phosphors for electroluminescent display panels comprising CuS coated ZnS:Mn phosphor powder bonded in an organic dielectric binder. By providing 2 to 12% by weight silver (Ag) in the CuS coating, and 0.1 to 3% by weight element sulfur (S) in the dielectric binder, the operating life of the phosphor material is increased.

ZnO:Mn.

The test surface containing the phosphor particle reporters may be excited to phosphoresce by use of suitable electromagnetic radiation. The test surface may be part of a wave guide which carries the electromagnetic radiation such that any phosphor particles adjacent the test surface will be excited by the radiation travelling along the wave guide to emit detectable phosphorescence. Examples of phosphor materials are described in U.S. Pat. Nos. 4,830,875; 4,879,186; 5,122,305 and 5,227,254. A further benefit in using phosphor particles is that their composition may be selected in a way to determine the colour of the phosphorescence:

| Colour | | Metal Selection |
|--------|---|----------------|
| Red | - | CdS:Eu |
| Green | - | ZnS:Tb, F |
| Blue | - | SrS:Ce, K |
| White | - | SrS:Ce, K, Eu and SrS:Pr, K |

It is also possible to select micron and nano size particles which have two or more of the dielectric properties, paramagnetism and phosphorescence. Such combination of properties in the particles may be advantageous in providing a cross-check of the biosensors sensitivity and operation.

A category of viruses is the phage and in particular the bacterial phage. In accordance with the technology described in U.S. Pat. No. 5,403,484, Ladner et al. provide phage particles which can express on their surface engineered binding domains for target molecules. The target molecules may be biological or synthetic macromolecules as well as other organic and inorganic substances. The phage particles by virtue of their protein structure have dielectric properties. Phage particles are commonly of nanometer size usually in the range of 10 to 30 nm. Phage particles may be selected which have the desired dielectric constant usually of about 3, for use in this invention as reporter particles in a capacitance biosensor. Considering that water has a dielectric constant about 81, the dielectric constant of a phage renders it quite useful in this invention. Phages behave as very high molecular weight proteins in solution and therefore can be caused to move in an electrophoretic field—this being advantageous for separation from the surface of the capacitor. In addition to the phage particles being engineered to express on their surface desired binding domains, the phage particles may also include DNA sequence information which when expressed provide reporter material on the surface of the phage, for example, proteinaceous material which may have phosphorescent properties. Hence, the phage particles may be used in the assay system as a bifunctional particle. The phage particles may also be engineered to express binding domains which attract iron entities thereby rendering the phage particles paramagnetic. The phage particles can therefore be used as particle reporters either as particles having inherent dielectric properties or engineered to have one or more of dielectric properties, paramagnetic properties and phosphorescent properties. The phage particles can be disrupted, their nucleic acid material removed, and then repackaged around a solid-phase phosphor dielectric and/or paramagnetic nanoparticle by the methods generally outlined in Kossovsky's U.S. Pat. No. 5,219,577.

A significant advantage in using engineered phage particles is that the phage particles in expressing binding domains on their surface to target molecules can then be designed to bind to the targeted analyte, the recognition molecules or the analyte entities. Phage particles inherently provide the nanometer size along with the engineered ability to present binding domains which effectively replace any steps needed in respect of other types of nanoparticles in linking the phage particles to the recognition molecules, target analyte or analyte entities. Considerable flexibility is provided in use of phage particles in designing the assay whether it be competitive, sandwich, direct or indirect type of assay. It is also understood that the phage particles may be used in combination with the other types of nanoparticles to provide more than one system in evaluating presence or absence of the reporter phage particles.

Certain theoretical considerations are necessary for discussing in detail the capacitor sensors as shown in the Figures. The capacitance of a parallel plate capacitor in which the region between the plates is filled with vacuum (free space) is $$C = Q/V = A * \epsilon_o / d \tag{1}$$

where Q is the charge in Coulombs, V is the voltage between the plates, A is the area of the plates in square meters, and d is the distance between the plates in meters, and $\epsilon_o$ is the permittivity of free space ($8.85 * 10^{-12}$ coulomb$^2$/Newton-Meter$^2$).

For capacitors in series the total capacitance is expressed as $$1/C = 1/C_1 + 1/C_2 + \ldots + 1/C_n \tag{2}$$

Matter is polarized to varying degrees such that the permittivity ($\epsilon$) is a multiple of that of vacuum ($\epsilon_o$).

$$\epsilon = K * \epsilon_o$$

or $$K = \epsilon / \epsilon_o \tag{3}$$

Where K is the dielectric constant.

$$C = (\sigma_f * A) / (E * d) \tag{4}$$

Where $\sigma_f$ is the charge density ($Q_f/A$) of free space, E is the applied electric field, and d is the distance between the parallel plate conductors.

$$E = (\sigma_f + \sigma_p) / \epsilon_o \tag{5}$$

Where $\sigma_p$ is the polarization charge density due to the electric dipole charge displacement.

$$\sigma_f = \epsilon_o * (1 + \chi) * E \tag{6}$$

$$P = \epsilon_o * \chi * E \tag{7}$$

Where P is the dielectric polarization field, and $\chi$ is the dielectric susceptibility of material.

$$C = (\epsilon_o * (1 + \chi) * A) / d \tag{8}$$

$$K = (1 + \chi) \tag{9}$$

$$C = (\epsilon_o * K * A) / d \tag{10}$$

Equation 10 relates the capacitance (C) surface area (A), and separation distance (d) of the "plates" of the parallel plate capacitor model, and to the dielectric constant (K) of the material filling the space between the plates.

According to equation 2, if the space between the plates of the capacitor is filled with two different dielectric materials having thickness $d_1$ and $d_2$ respectively and dielectric permittivities of $\epsilon_1$ and $\epsilon_2$ respectively, then the capacitance is expressed as:

$$C = \epsilon_o * A / (d_1/\epsilon_1 + d_2/\epsilon_2) \tag{11}$$

Both Newman U.S. Pat. No. 4,822,566 and Bataillard [Bataillard et al., *Anal. Chem.* (60):2374–2379, 1988] relate measurement of capacitance change to the change in effective dielectric constant, and effective thickness of the dielectric layer upon complex formation between the analyte and the recognition molecule. This theory is recast in terms of dielectric particles for the purposes of the present invention. Functionally, water either occupies or is displaced from a layer whose thickness is determined by the effective diameter of the dielectric particles—including the linker and attached analyte or recognition molecules. If the dielectric particle itself has a diameter much larger than that of the bound molecules (as would be the case for such drugs as phenytoin, digoxin, cyclosporin and FK-506), then the dielectric constant of the particle makes the dominant contribution to the measured change in capacitance. If the attached molecules and the particle have similar diameters, then the effective dielectric constant will lie between that of the attached molecules and that of the particle. Finally, if the attached molecules have a much greater diameter than that of the particle, then the dielectric constant of the molecules will make the dominant contribution to the measured change in capacitance.

For the purposes of the following discussion it is assumed that water is by far the most abundant species in a sample, and that its dielectric constant dominates the net dielectric constant of the sample. In real samples, high protein and lipid species concentrations may shift the net dielectric constant of the undiluted sample toward the value of 1 by an unknown amount.

The "plates" or metallizations forming the plates of the capacitor are covered with a water- and electrolyte-impermeable passivation layer of thickness $d_p$ and dielectric constant $K_p$. The two layer dielectric model of equation 11 is therefore applied. The analyte and recognition molecule then form a complexing layer attached to this passivation layer, dielectric particles being either added to or displaced from this layer. If water (subscript w) exchanges with a dielectric layer (subscript d), the change in capacitance is described by two conditions:

$$1/C_1 = (d_p/K_p + d_d/K_d)/(\epsilon_o * A) \quad (12A)$$

$$1/C_2 = (d_d/K_p + d_d/K_w)/(\epsilon_o * A) \quad (12B)$$

Where $C_d$=Capacitance of the complexing layer with dielectric particles $C_w$=Capacitance of the complexing layer with water in place of particles $d_d$=Effective thickness of the dielectric layer (approximately the diameter of the dielectric particles for small analysis and recognition molecules)

$d_p$=Thickness of the passivation layer over conductors (plates) of the capacitor (eg. $SiN+SiO_2$)

A=Area of capacitor plates $K_d$=Dielectric constant of particles $K_w$=Dielectric constant of water $K_p$=Dielectric constant of passivation layer The thickness of the water layer is the same as that of the dielectric particle layer with which it exchanges. Thus it can be seen from equations 12A and 12B that the change is determined exclusively by the change in dielectric constant $K_d$ to $K_w$ in the complexing layer. If is also seen, that for a capacitive sensor with a given plate area (A), the sensitivity is increased by having a passivation layer with high dielectric constant ($K_p$), and minimal thickness ($d_p$), to make the term $d_p/K_p$ as close to zero as possible. In practice, defect or pinhole-free passivation layers of silicon nitride must be more than about 100 nm thick. Polymer coatings, such as parylene or polyimide, may be 1 micron or more in thickness to guarantee pinhole-free surfaces. Overlaid upon these is a $SiO_2$ layer of approximately 100 nm thickness to provide for covalent immobilization via an aminoalkylsilyl or thiolalkylsilyl linker. The resulting passivation layer may therefore be expected to be about 300 nm or more in thickness in practical devices.

To optimize the capacitive sensor device design, various practical values were substituted into equation 12 for the parameters $d_p$, $d_d$, $K_p$, $K_d$ and $K_w$. The model calculates the maximum expected change in capacitance which would occur if a dense dielectric layer of nanoparticles 300 nm in diameter (thick) exchanged with a water layer 300 nm thick. The maximum delta C is achieved with the thinnest possible passivation layer having the highest possible dielectric constant (eg. a ferroelectric ceramic such as $BaTiO_3$), and dielectric nanoparticles having a dielectric constant as close as possible to 1.

The advantage of this invention is that:

1. the dielectric constant of the label/tag is chosen to be optimally different from that of the buffer medium to effect the maximum capacitance/permittivity change of each molecule exchanged/displaced.

2. the dielectric label/tag may be made arbitrarily large relative to the analyte or recognition molecule such that one can control the "quantum" change in measured capacitance for each molecular recognition or binding event. That is each label/tag particle can be made to exchange with an arbitrarily large number of buffer molecules.

3. the dielectric label/tag can be selected to contribute the dominant dielectric constant in the complex (analyte-recognition molecule-dielectric label/tag) thereby minimizing the analyte-to-analyte, assay-to-assay variation which is in inherent in the analyte-recognition complexes themselves.

This permits more uniform instrumental design, assay chemistry and sensor device manufacturing processes.

Figure 3:
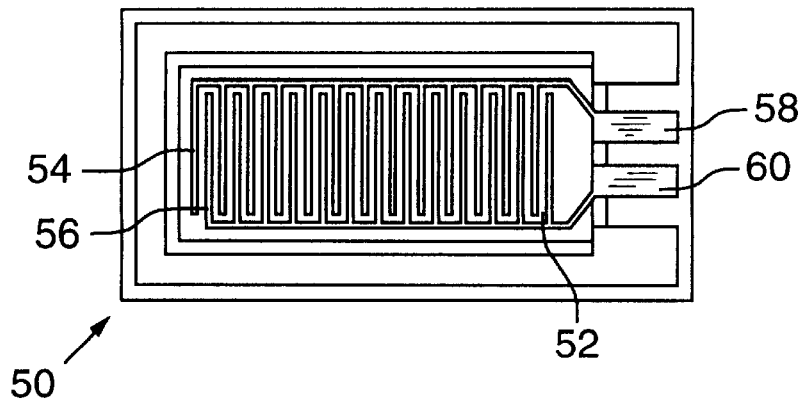
FIG. 3 is a top view of a capacitance sensor.
Figure 4:
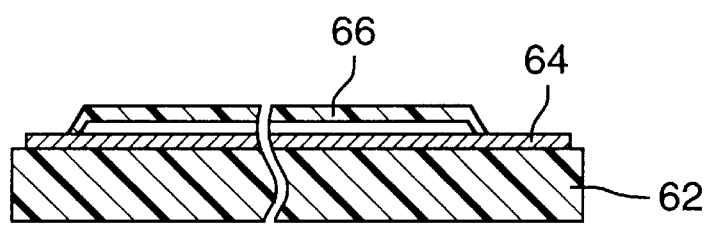
FIG. 4 is a section through the sensor of FIG. 3.

In accordance with one aspect of the invention, a test component of a capacitance biosensor for use in a suitable diagnostic apparatus is shown in FIGS. 3 and 4. The test component 50 has a test surface 52 with capacitor electrodes 54 and 56 along the length of the test surface where the electrodes 54 and 56 may be oppositely charged through circuit contacts 58 and 60. The electrodes and circuit contacts may be laid down on a quartz, i.e., silica substrate 62 where they may be deposited by chemical vapour deposition on a grown layer of silica on a silicon wafer. The electrodes may be of titanium plus or minus gold metallization layer etched to produce the electrodes or plates of the capacitor thereby achieving a large face area with interdigitating structure. Laid over top of the metallization layer is a passivation layer which may be of silicon nitride. The passivation layer is a pin hole defect-free dielectric passivation layer which may be approximately 300 nm thick. The dielectric passivation layer as laid over the metal plates prevents sample and reagents from permeating to or reacting with the electrodes. As shown in FIG. 4, the dielectric passivation layer is indicated at 64. On top of the passivation layer is a further dielectric layer which may be, for example, of silicon dioxide. The layer 66 may be approximately 200 nm thick. The purpose of the outer silicon dioxide layer is to facilitate linking of the recognition molecules or other bioactive molecules to the surface. The layer 66 is hot an integral requirement of the capacitance biosensor other than to provide this surface for covalent linking or other type of linking or mobilization of the bioactive molecules to the surface of the sensor. As described in Newman U.S. Pat. No. 4,822,566, the linker molecule as attached to the outer $SiO_2$ layer 66 may be designed to space the bioactive molecules away from the electric double layer of the sensor to enhance the base and test signals of the device. An advantage of the first and second dielectric layers 65 and 66 which has not been apparent in prior biosensors, is that these layers have the ability to amplify or attenuate the sensitivity of the device. Layers 64 and 66 should be as thin as possible for best sensitivity. A ferroelectric layer of barium titanate may be much thicker and still provide high sensitivity. Elimination of the outer dielectric layer may increase sensitivity. Other considerations include particle diameter varying sensitivity. The particle dielectric constant should be as different from that of the sample buffer as possible. Preferably the dielectric particle has a dielectric constant K as close to one as possible rather than a very high dielectric constant K such as in a ferroelectric particle.

Figure 12:
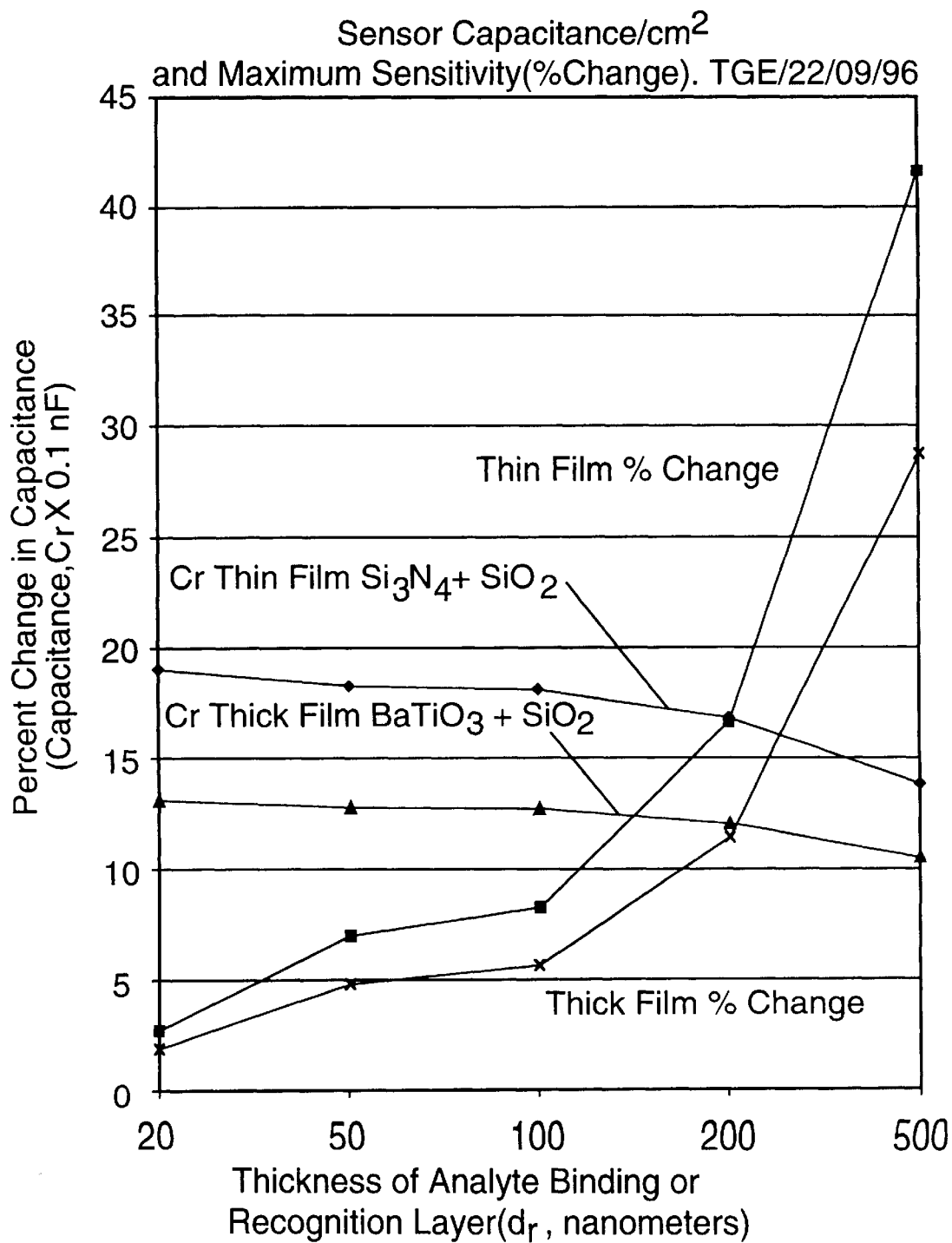
FIG. 12 is a plot of sensor capacitance vs. sensitivity with glass passivation.
Figure 13:
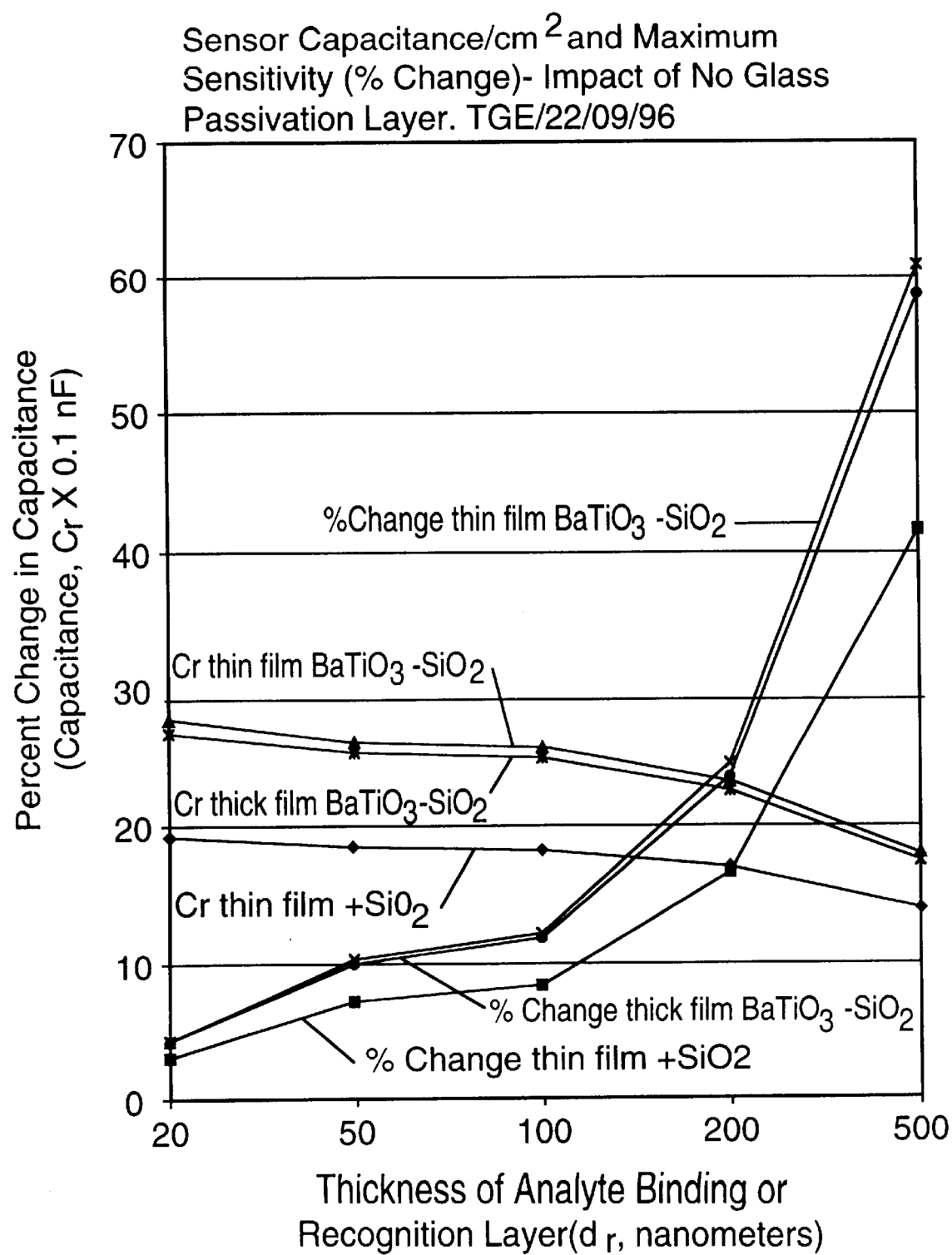
FIG. 13 is the same plot without glass passivation.
Figure 14:
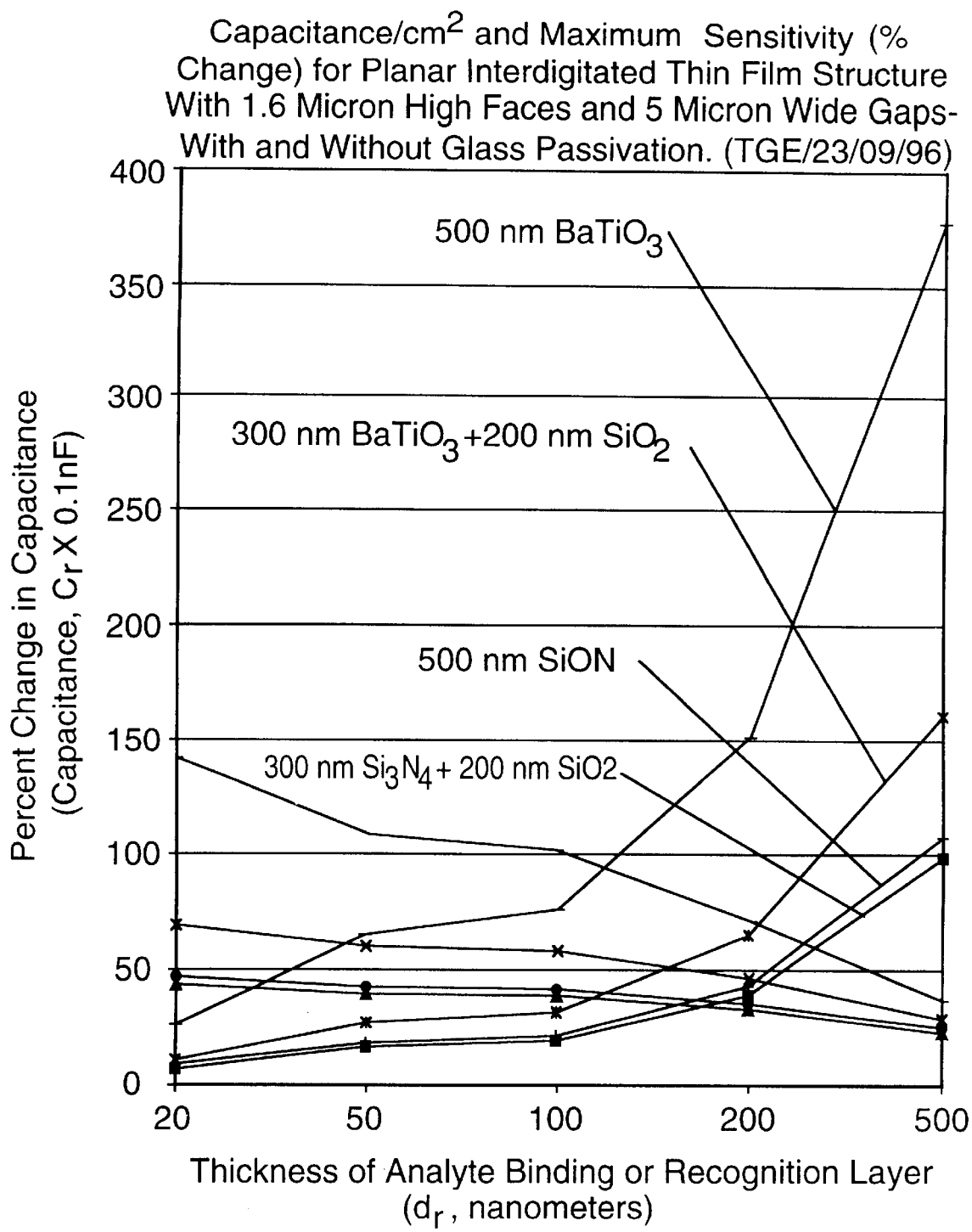
FIG. 14 is a plot of capacitance vs. sensitivity for the thin film planar interdigitated capacitance biosensor.

FIG. 12 shows how capacitance and percent change in capacitance (sensitivity) are related to particle diameter. A thin film device having 300 nm of $Si_3N_4$ (K=8) plus 200 nm $SiO_2$ (K=6) has about 50% higher sensitivity than a thick film device with 25000 nm of $BaTiO_3$ (K=4500) and 1000 nm of $SiO_2$. FIG. 13 shows how replacing the $Si_3N_4$ of the thin film device with $BaTiO_3$ and removing the glass layer of each of the thin and thick film devices improves sensitivity again, the thick film device becoming equivalent to the thin film device. An important consideration for a single thin or thick layer of $BaTiO_3$ is that the layer is passive, and impermeable to sample, and capable of derivatization. FIG. 14 shows these effects again for a thin film structure with coplanar interdigitated capacitor "plates".

The advantage of nanoparticle-tagged reporters over the unaided molecular complex detection approach of previous work is better uniformity of method for different analytes. Because there is a large "quantized" dielectric change per particle bound to or removed from between the "plates" of the capacitor, calibration and test formatting is less influenced by the great variation in molecular dimensions between steroid hormones and immunoglobulins for example. One should choose particle size to give the highest sensitivity while at the same time retaining the ability of the particles to be dispersed and interact homogeneously with the sample analyte.

Methods for forming thin and thick films of ferroelectric materials at low temperature have been improved steadily. Much of the work in the field was reviewed at the 1996 Spring Materials Research Society Meeting (Apr. 7–12, 1996, San Francisco Marriott). Known high dielectric constant inorganic titanates, niobates, and ferroelectric polymers can be formed by many processes including low temperature chemical vapour deposition, laser photoablation deposition, sol-gel processes, RF magnetron sputtering, screen printing/and firing, and spin coating (in the case of the polymer). The more common electronic materials are the BST (Barium-Strontium-Titanate), PZT (Lead-Zirconium-Titanate), and lead niobate groups. It is thus possible in the case of $BaTiO_3$, for example, to screen print a low firing temperature paste compatible with 70Ag/30Pd metallization forming 10 to 25 micron layers on thick film substrates (K-4400 X7R, MRA Laboratories, North Adams, Mass.). This gives thick film devices a performance equivalent to integrated circuit or thin film devices. In addition, it is possible to form printed circuit traces on 25 micron copper-clad laminate flexible films or injection molded devices of Kapton (polymer). These may also be overlaid at low temperature with ferroelectric BST and PZT films and glass passivation layers.

Other recently developed electronic materials processes may advantageously apply to the fabrication of capacitive biosensors. For example, photo-ablative Eximer, YAG and $CO_2$ laser etching and micromachining of metal-clad plastic laminates, ceramic ($Al_2O_3$) substrates, conventional PC board materials, polyimide, and conformal coating resins are available (e.g. Lumonics Inc., Ottawa, Ontario, Canada). Sharp features can be maintained at dimensions compatible with thick film (channels 25 microns deep by 50 microns wide). Additional laser processes include package welding, mold machining, and semiconductor/ceramic film deposition and annealing.

Figure 5:
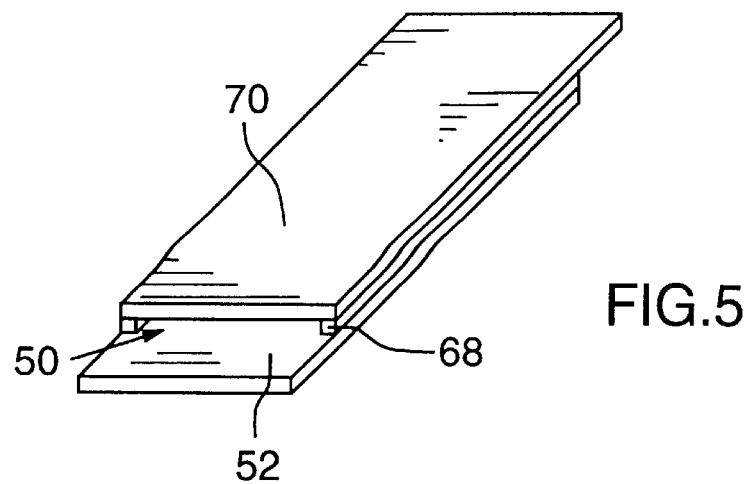
FIG. 5 is a perspective view of the capacitance sensor of FIG. 3 having a capillary for a volume of the sample space provided thereon.

FIG. 5 demonstrates the manner in which the test component of FIG. 3 may be adapted for sample injection. The test component 50 may have along each side spacer elements 68 to support above the test surface 52, a second plate 70. The element 68 may be of nominal size, such as 25 microns to define a capillary space which attracts the sample to within the device so that the presence or absence of analyte may be detected across the face of the test surface 52.

Figure 6:
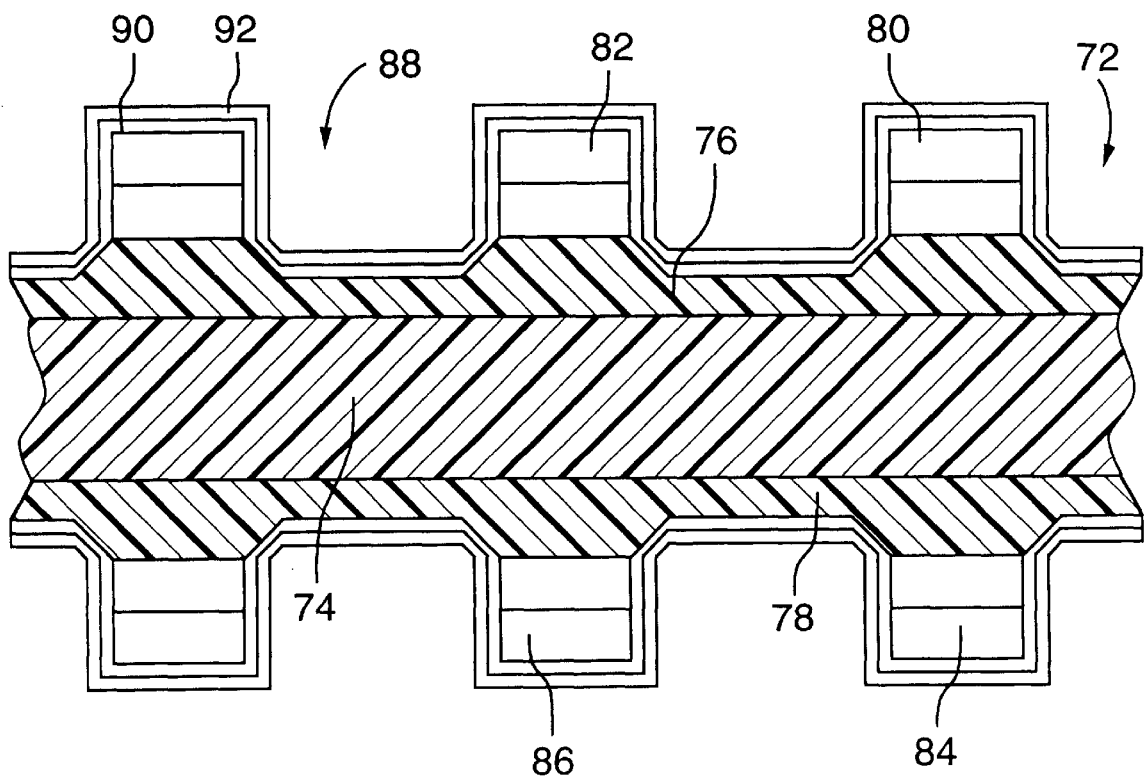
FIG. 6 is a section through an alternative structure for the capacitance sensor.

FIG. 6 is a section through an alternative structure for the test component of the biosensor. The test component 72 has a central silicon substrate 74 with grown silica layers 76 and 78 on opposite surfaces of the substrate 74. As with the device of FIG. 3, spaced apart electrodes 80 and 82 which may be oppositely charged and 84 and 86 on the other side of the device which may be oppositely charged. The electrodes are formed to be raised relative to the surface of silica layers 76 and 78 to define mini-wells or channels. The electrodes and mini-wells are covered with the dielectric layer of, for example, barium titanate or silicon nitride 90. On top of layer 90 is the outer layer 92 of silica which facilitates covalent linking to the desired molecules and optionally to increase sensitivity of the device. This outermost layer is 92. Suitable metal contacts are provided in the test component to oppositely charge the electrode sets 80 and 82 and 84 and 86 along the width and length of the test surface.

Figure 7:
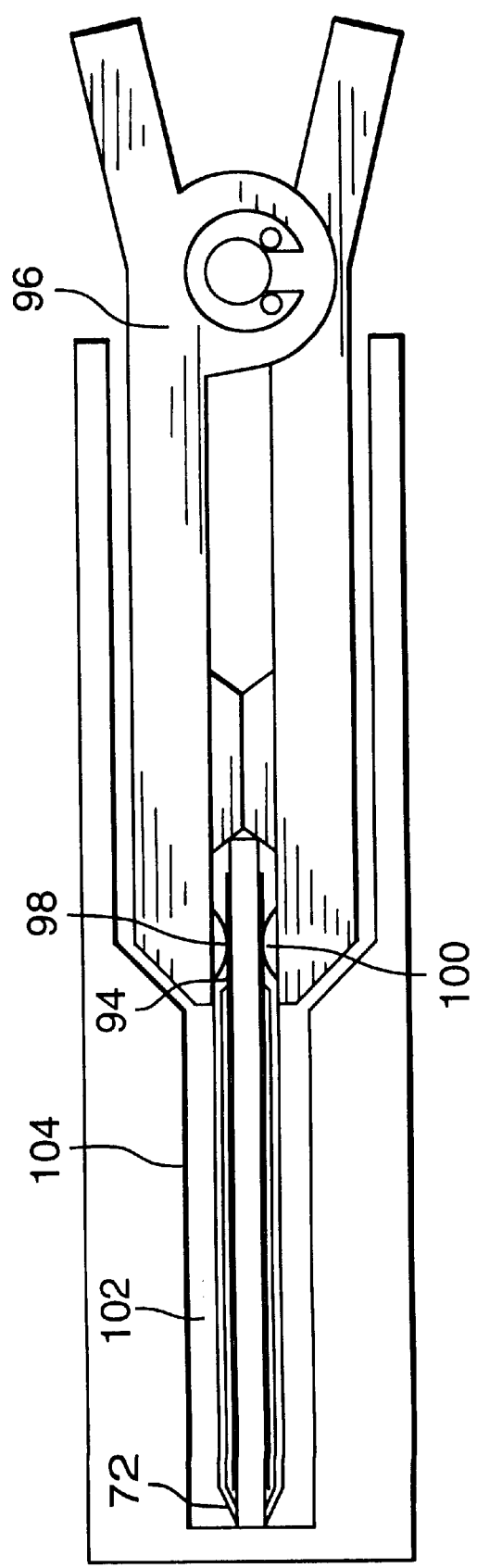
FIG. 7 shows the robotic arm gripping the capacitance sensor of FIG. 6.

A significant advantage of the dual sided device is to provide a reference or control in conducting the test. As shown in FIG. 7, the test component 72 may be gripped at its end portion 94 by a robotic gripper device 96. The robotic gripper device may include electrodes 98 and 100 for charging as desired the electrodes 80 and 82 and 84 and 86 on each side of the device. The sample 102 to be tested is contained within a sample containing cuvette 104 where readings may be taken for the base signal and the test signal and depending upon formations on the opposite sides, provide an accurate quantitative answer for the determination of analyte in the sample.

The capacitor biosensor could be fabricated in silicon, by thin film techniques. It would appear essentially the same and have approximately the same surface area if it were fabricated by either printed circuit or thick film techniques. A double-sided structure maintains intimate thermal contact between active devices. One side is the reference device in a differential sensor arrangement so that temperature-induced noise or background is minimized. A commercial 3-axis pipetting robot (Diamedix, Tecan and Beckman are manufacturers of such sample processing robots) with a solenoid-actuated gripper precisely positions the sensor, and makes circuit contact. Preamplifiers and other components may be incorporated into the gripper if required to improve signal-to-noise ratio.

All three manufacturing approaches require printing, or deposition of a high dielectric constant ferroelectric material such as $BaTiO_3$ over the metallization layer, and optionally, depositing silica or silicon oxynitride over the ferroelectric.

Figure 8:
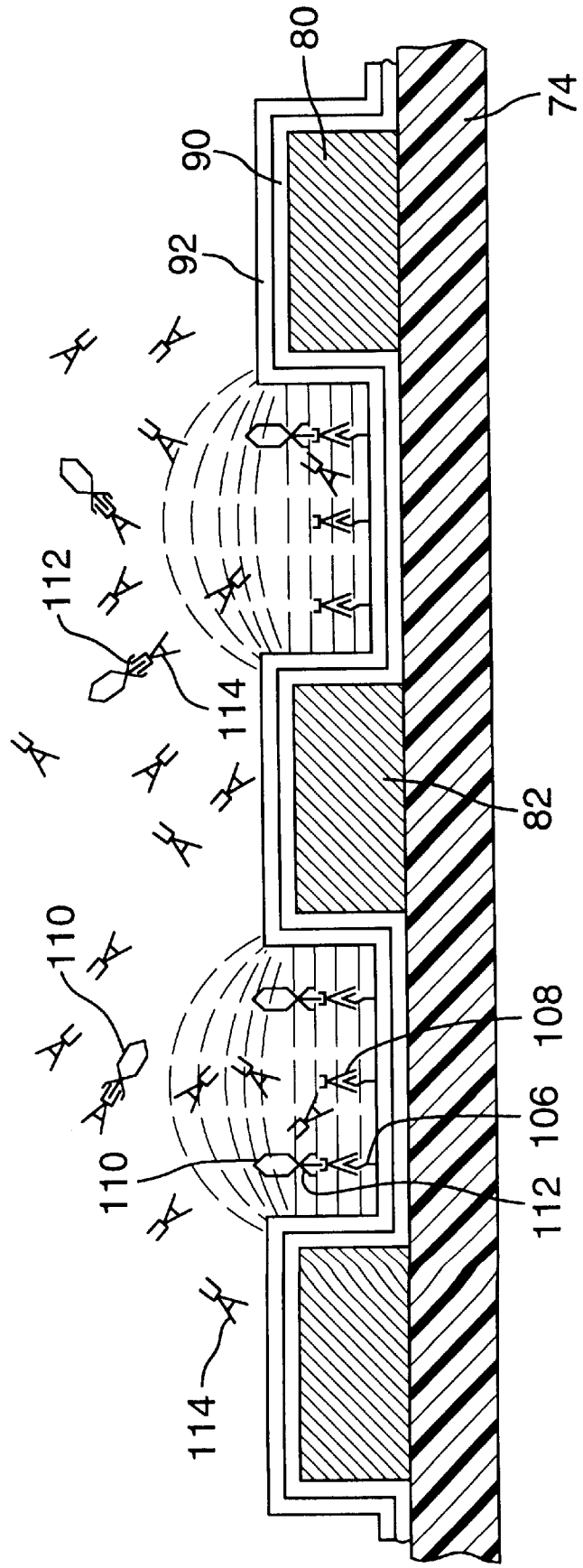
FIG. 8 is a section through an alternative capacitance sensor surface commonly referred to as an open face capacitor for detecting presence of absence of phage reporter particles.

FIG. 8 is an enlarged view of a proposed competition reaction using the device of FIG. 6. In FIG. 8 the quartz substrate 74 has the electrodes 80 and 82 provided thereon of oppositely charged polarity and the dielectric layer 90 is covered with the linking layer 92. Linking molecules 106 link the analyte entities 108 to the surface 92. Phage particles 110 have recognition molecules 112 expressed on their surface which recognize either the analyte entities 108 or the analyte 114 of the sample. When the sample is introduced to the test surface, the analyte molecules 114 compete with the analyte entities 108 for the recognition molecule site of the phage 110. This competition forms a complex of the phage particles 110 by virtue of their recognition molecules 112 binding to the analyte 114. Such competition removes the phage particles 110 from the test surface. By removal of such analyte particles from the test surface, the capacitance of the device has changed and hence, a measure of the amount of analyte in the sample can be detected by use for example, of the biosensors of FIGS. 10 and 11.

The sensor for sensing phosphorescence from solid-state phosphor particles may be constructed in accordance with standard phosphorescence sensing technology. The phosphorescence sensor device is comprised of a solid phase upon which is attached a primary recognition molecule which specifically complexes with the analyte to be measured. The device requires, in addition, a light source (such as a Xenon flash lamp, laser diode, LED) or pumping source (such as an electron beam, or electroluminescent mechanisms) and a sensitive light detector (such as a photomultiplier, microchanel plate, or avalanche photodiode). The method of attachment of the primary recognition molecule is preferably by covalent binding via a linker; and the solid phase may be of any material, preferably one which may be derivatized to permit the said covalent binding process. The sensor/assay reporter is comprised of phosphorescent microparticles or nanoparticles which are covalently attached to either analyte molecules or chemical analogs of the analyte molecules or a secondary recognition molecule via a second linker. The phosphorescent micro- or nanoparticles are of water-insoluble ceramic, glass, doped-glass, inorganic or organic phosphor-loaded polymer, and may have dielectric constants suitable for capacitance detection or dielectrophoretic field migration and concentration. The solid phase may take the form of a bead or particle (a carrier), a mesh, a surface providing part of a container for the sample and assay reagents, or an optical waveguide. The optical waveguide may allow source light "evanescent wave" excitation of the phosphorescent micro- or nanoparticles which have been complexed with the primary recognition molecule and held within a few wavelengths of the surface. Further, the optical waveguide may provide efficient collection of the phosphorescent light emission and focusing thereof on the phosphorescence detector. For the best signal to noise ratio, the light source will be pulsed or chopped and have a "turn-off time" much shorter than the half-life of the phosphorescence of the reporter. In addition, the detector will be blocked or electronically gated off during the ON period of the light source, then unblocked, or gated on during the OFF period of the light source.

The phosphorescence sensor exploits the trapped electron or excited states of room temperature phosphorescent materials. The delayed emission of the excited triplet state of phosphors typically ranges from microseconds to milliseconds as compared to the prompt radiative electron transition of fluorophores which takes place in typically less than 20 nanoseconds. This characteristic of phosphors permits the synchronous "gating" of the detector. That is, while the high intensity of the light source is applied to excitation of the phosphor-labelled material the light path to the detector is blocked (eg. by a chopper or other fast-acting electromechanical device) or the detector is electronically gated off (eg. grid-gated photomultipliers). Thus background light, due to source light scattered from the surfaces of the container, macromolecules or colloidal substances, and prompt fluorescence of sample and buffer proteins and sensor device materials, is blocked from reaching the detector or contributing to the detected signal. Conversely, when the source is blocked or electronically turned off, the detector is unblocked (gated on) and can "see" only the phosphorescent signal without background contributions. This is a classical phosphorimetry method which affords the highest signal-to-noise ratio in the instrument measurement of the fluorescence/phosphorescence.

Solid state ceramic, doped glass, and porphyrin-derivative-loaded polymeric materials may be excited by relatively inexpensive and commercially available light sources. For example, Hammamatsu manufactures long life low electronic noise Xe flashlamp modules, and SiC LESs producing 480 nm blue light and 410 nm near UV light output have been fabricated by Sapphire Research and Production Amalgamation (Moscow, Russian Republic).

Figure 9:
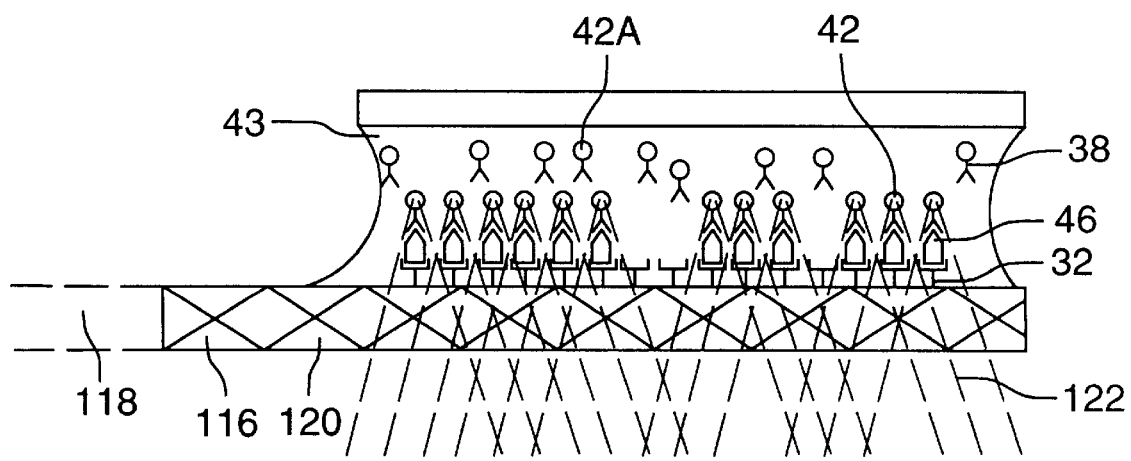
FIG. 9 is an illustrate example of evanescent wave excitation of solid state phosphor particles.

More specifically, the sensor device of FIG. 9 involves the evanescent wave excitation of the phosphorescent micro or nanoparticles. The test component may be of the type described with respect to FIG. 2 where the recognition molecules 32 form a complex with the analyte 46 and the labelling entities 38 which carry the phosphor particle 42. The excitation radiation is projected at the waveguide 116 which may be the silica substrate. The radiation enters in the form of a direct beam 118 and travels along the waveguide 116, as indicated at 120. In accordance with evanescent wave excitation, the radiation as it travels along the surface of the waveguide 116 only excites the phosphorescent particles 42 bound to the complex of the recognition molecule 32 with the analyte 46. Hence, the particles 42 emit radiation, as indicated by lines 122, whereas the particles 42A, which are not bound to the surface and free in solution, are not affected by the radiation and hence do not phosphorescence. A suitable device as described with respect to FIG. 11 is then used to detect the phosphorescence 122 and provide a quantitative determination of the amount of analyte 46 complexed with the recognition molecules 32.

Figure 10:
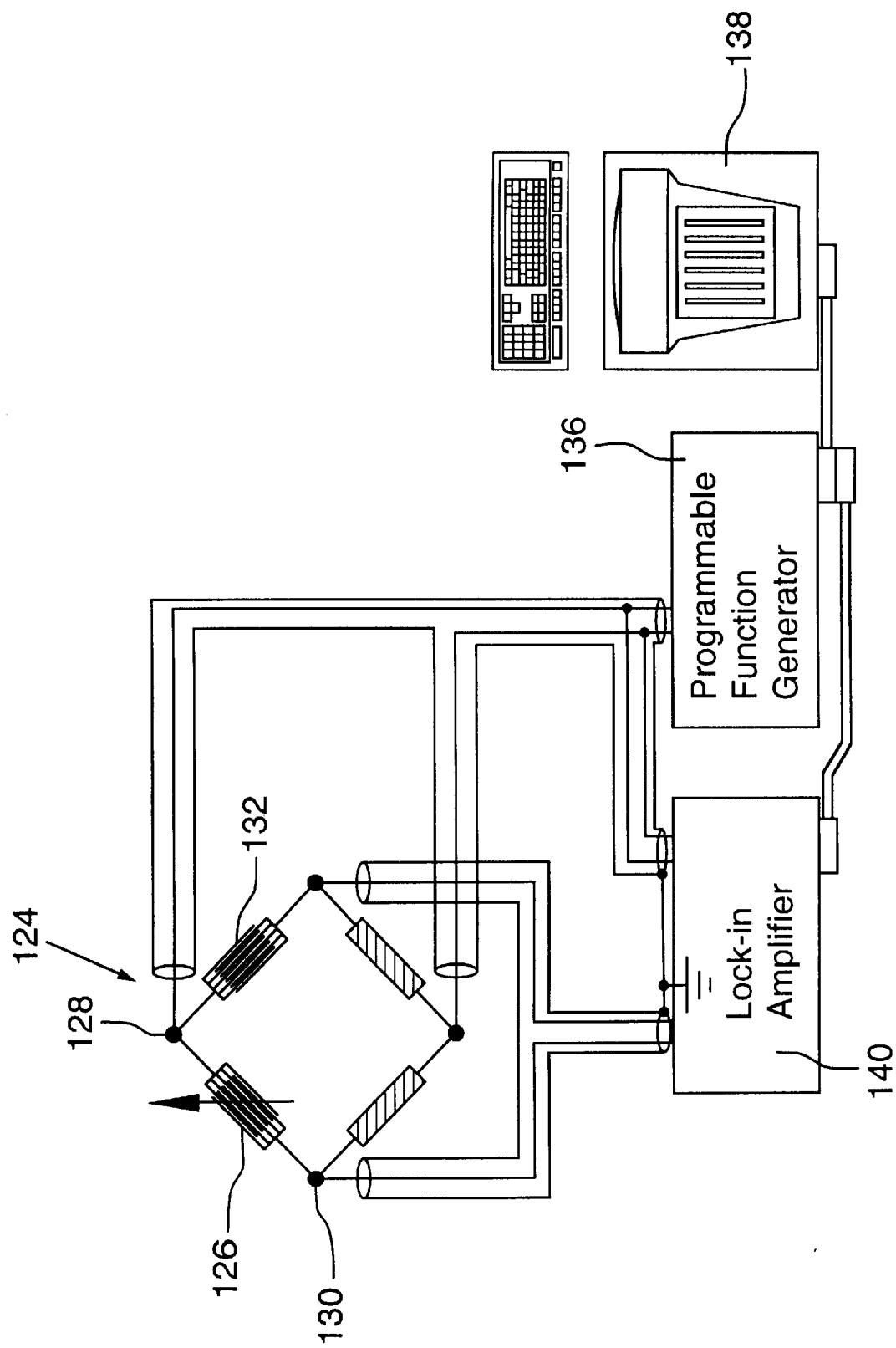
FIG. 10 is a block diagram view of the instrumentation for measuring reactants in capacitance sensor.
Figure 11:
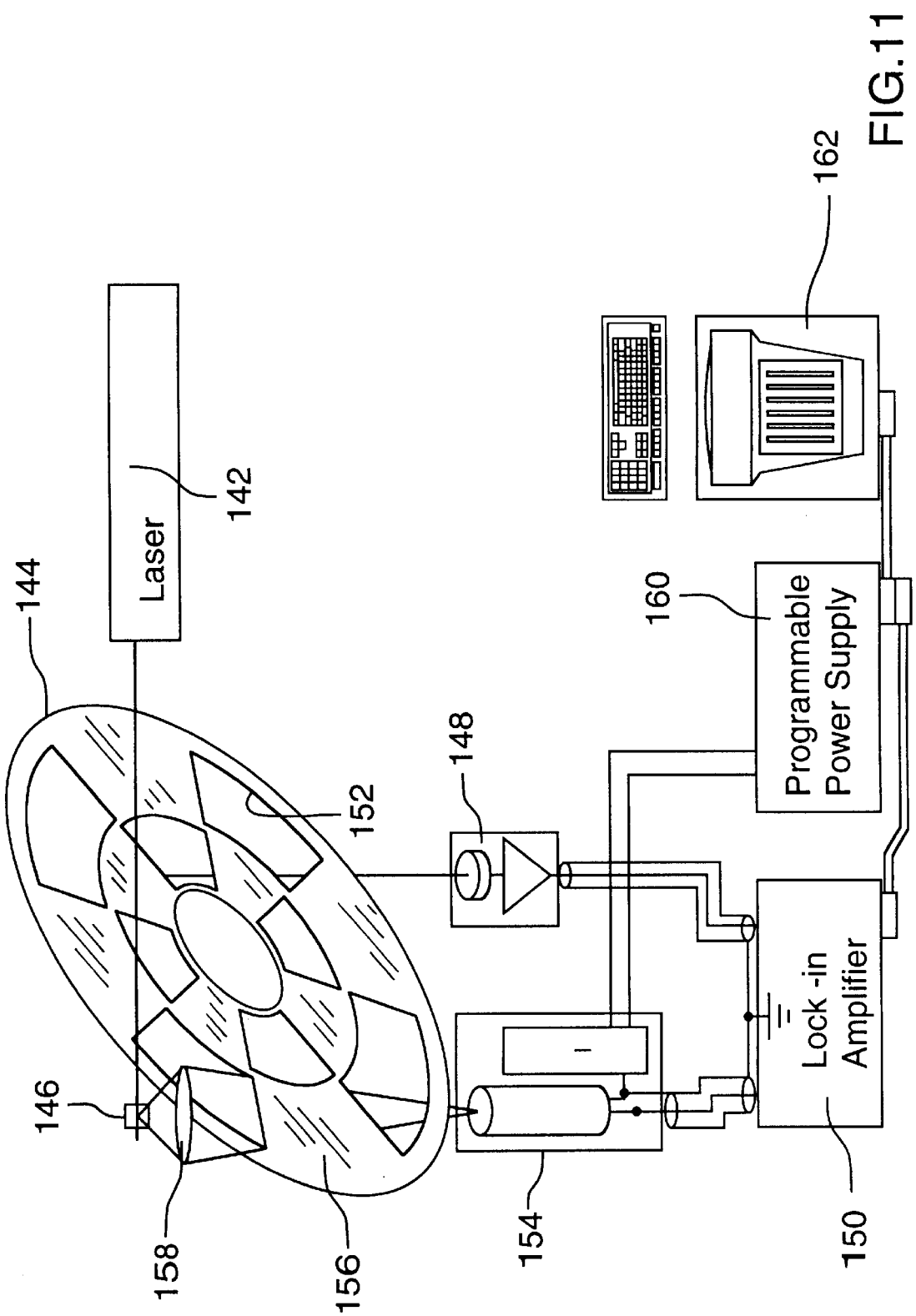
FIG. 11 is a block diagram of instrumentation used in measuring phosphorescence from a solid state or solid phase phosphor particle based labelling entity.

FIGS. 10 and 11 provide block diagrams of the devices for sensing capacitance or phosphorescence. FIG. 10 shows a test instrument configuration for measuring differential changes in sensor capacitance due to analyte-related addition or removal of dielectric particles between the "plates" of the capacitor sensor under test. The Wheatstone Bridge 124 circuit permits the measurement of voltage amplitude and phase differences between the active device 126 under test in one arm of the bridge between electrodes 128 and 130 and an identical capacitance device 132 with ionizing radiation inactivated or crosslinked recognition molecules in the opposite arm of the bridge between electrodes 128 and 134. Thus the reference capacitor 132 compensates for such variables as temperature, sample protein concentration, lipemia, drugs, and other interference factors which may alter the device response to the analyte concentration.

The bridge excitation voltage, waveform, and frequency may be downloaded to the programmable function generator 136 (Stanford Research Systems DS345-01) under computer 138 software control (National Instruments Lab-Windows/CVI) via an IEEE 488.2 or GPIB interface (National Instruments PCI bus interface 777158-51). As an alternative, for sine wave excitation only, the lock-in amplifier 140 (Stanford Research Systems SR830-DSP) can be remotely programmed for bridge excitation frequencies up to 100 KHz. Input range and filter settings are downloaded to the lock-in amplifier 140 digital signal processor, and in-phase and quadrature voltage data from the bridge circuit 124 is uploaded to the computer 138 for analysis via the IEEE instrument bus. The Stanford Research Systems Application Note #3, *About Lock-in Amplifiers* provides details on the sensitivity of impedance detection possible with digital signal processing lock-in amplifiers.

FIG. 11 shows in block form the instrumentation for measuring phosphorescence of solid-phase nanoparticles. The configuration is essentially that of a classical "phosphoroscope". A 6 mw helium cadmium laser 142 (Liconix) emitting at 340 nm wavelength is incident upon a high speed chopper wheel 144 (Stanford Research Systems SR540) which alternately passes the beam through to the sensor device 146 under test or reflects it to a reference photodiode (Hamamatsu photodiode-amplifier module G1957 148). The reference photodiode 148 thus receives pulses of laser light and produces output signal pulses to the lock-in amplifier 150 (Stanford Research Systems SR830 DSP) which are proportional in amplitude to the intensity of the laser pulses. These output pulses provide both a phase locking signal and a means for correcting phosphorescence measurements for variations in the exciting laser light intensity. Laser pulses passing through the chopper aperture 152 excite the nanoparticles while the view from the photomultiplier detector 154 (Hamamatsu H5773) to the test device 146 is blocked by a vane 156 of the chopper. Conversely, when the laser beam is blocked by the chopper 144 phosphorescence emission from the device 146 is focused through an aperture of the chopper onto the photomultiplier 154 via a high light collection efficiency lens 158. Thus the photomultiplier 154 and photodiode 148 signals are 180° out of the phase. In addition, the photomultiplier 154 is shielded from laser source scatter from the device thus permitting more sensitive detection. The scheme is applicable only to those phosphors which have half lives on the order of milliseconds. The photomultiplier 154 module contains an integral Cockcroft-Walton high voltage multiplier whose output is set by a low input voltage provided by the programmable power supply module 160 (Xantrex XT60-1). The sensitivity or gain of the photomultiplier may therefore be set under computer 162 software control (National Instruments Lab-Windows/CVI) via the IEEE 4888.2/GPIB interface with the programmable power supply. As in the case of the capacitance sensor test system of FIG. 10 input range and filter settings are downloaded to the lock-in amplifier-digital signal processor, and data from the detectors 148,154 is uploaded to the computer 162 for analysis via the same instrument bus. Stanford Research Systems Application Note #4, *Signal Recovery with Photomultiplier Tubes: Photon Counting, Lock-in Detection or Boxer Averaging* provides further information on the sensitivity of photomultiplier detection using lock-in amplifiers.

Although preferred embodiments of the invention have been described herein in detail, it will be understood by those skilled in the art that variations may be made thereto without departing from the spirit of the invention or the scope of the appended claims.

We claim:

1. A displacement competition assay for determining sample analyte concentration in a sample fluid, comprising:

(i) applying said sample fluid to a test surface having a binding agent bound through specific recognition sites to an immobilized analyte, wherein said immobilized analyte is affixed to a solid support and said binding agent is labelled with phages encapsulating reporter particles, said reporter particles providing a base level signal; and (ii) binding said sample analyte to at least one of said specific recognition sites wherein binding of said sample analyte to said specific recognition site displaces said labelled binding agent away from said test surface into said sample fluid to define a test level signal, wherein displacement of said labelled binding agent is related to the concentration of sample analyte in said sample fluid;

(iii) removing said sample fluid from said test surface; and (iv) comparing said base level signal to said test level signal to determine the concentration of said sample analyte.

2. The competition assay of claim 1, wherein said labelled binding agent and said sample analyte form a complex and wherein said complex is displaced into said sample fluid.

3. The competition assay of claim 1, wherein said test surface is provided on one or both of two parallel plates spaced apart at a distance so as to effect capillary movement of said sample fluid across said test surface.

4. The competition assay of claim 1, wherein said reporter particles are paramagnetic, said test level signal being measured in inductance when said test surface is exposed to a magnetic field.

5. The competition assay of claim 1, wherein said reporter particles are dielectric, said test level signal being measured in capacitance when said test surface forms part of a capacitor.

6. The competition assay of claim 5, wherein said test surface comprises a ferroelectric layer.

7. The competition assay of claim 6, wherein said ferroelectric layer comprises barium titanate.

8. The competition assay of claim 1, wherein said reporter particles have at least one of a dielectric, magnetic or phosphorescent property.

9. The competition assay of claim 1, wherein said reporter particles are phosphorescent, said test level signal being detected as phosphorescent radiation when said test surface is stimulated to cause said particles to phosphoresce.

10. The competition assay of claim 1, wherein said reporter particles are individually in the range of 1 to 1000 nanometers.

11. The competition assay of claim 1, wherein said reporter particles are individually in the range of 1 to 1000 microns.

12. The competition assay of claim 1, wherein said phages encapsulating reporter particles express on their surface said binding agent and are reversibly bound through specific recognition sites to said immobilized analyte, and wherein said sample analyte competes with said binding agent for recognition sites on said immobilized analyte and displaces said phage particle, wherein displacement of said phages encapsulating reporter particles defines a test level signal.

13. The competition assay of claim 1, wherein said phages encapsulating reporter particles express on their surface said binding agent and bind reversibly to specific recognition sites on said immobilized analyte, and wherein said sample analyte competes with said immobilized analyte for recognition sites on said binding agent and forms a complex with said binding agent to displace said phage particle from said test surface, wherein said phages encapsulating reporter particles and sample analyte complex defines a test level signal.

* * * * *